(12) United States Patent
Fukamachi et al.

(10) Patent No.: US 12,090,312 B2
(45) Date of Patent: Sep. 17, 2024

(54) ATRIAL ASSIST DEVICE

(71) Applicant: THE CLEVELAND CLINIC FOUNDATION, Cleveland, OH (US)

(72) Inventors: Kiyotaka Fukamachi, Cleveland, OH (US); Jamshid Karimov, Cleveland, OH (US); David J. Horvath, Cleveland, OH (US); Randall C. Starling, Cleveland, OH (US); Barry Kuban, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 621 days.

(21) Appl. No.: 17/285,584

(22) PCT Filed: Oct. 15, 2019

(86) PCT No.: PCT/US2019/056180
§ 371 (c)(1),
(2) Date: Apr. 15, 2021

(87) PCT Pub. No.: WO2020/081481
PCT Pub. Date: Apr. 23, 2020

(65) Prior Publication Data
US 2021/0393942 A1 Dec. 23, 2021

Related U.S. Application Data

(60) Provisional application No. 62/745,588, filed on Oct. 15, 2018.

(51) Int. Cl.
*A61M 60/00* (2021.01)
*A61M 60/165* (2021.01)
(Continued)

(52) U.S. Cl.
CPC ........ *A61M 60/165* (2021.01); *A61M 60/178* (2021.01); *A61M 60/216* (2021.01);
(Continued)

(58) Field of Classification Search
CPC .............. A61M 60/165; A61M 60/422; A61M 60/861; A61M 60/569
See application file for complete search history.

(56) References Cited

U.S. PATENT DOCUMENTS 4,994,017 A * 2/1991 Yozu ................... A61M 60/237
600/16
4,994,078 A * 2/1991 Jarvik ................. A61M 60/476
600/16

(Continued)

FOREIGN PATENT DOCUMENTS

WO 2012158543 A1 11/2012

OTHER PUBLICATIONS

PCT International Search Report and Written Opinion for corresponding International Application Serial No. PCT/US2019/056180, mailed Jan. 21, 2020, pp. 1-14.

(Continued)

*Primary Examiner* — Eric D. Bertram
(74) *Attorney, Agent, or Firm* — Tarolli, Sundheim, Covell & Tummino LLP

(57) ABSTRACT

A system for treating a patient with a heart condition includes an atrial assist device (AAD) configured to be positioned in the patients heart to pump blood from an atrium of the patients heart into a ventricle associated with the atrium. The system also includes a controller operatively connected to the AAD and being configured to control the AAD to pump blood from the atrium of the patients heart into the ventricle associated with the atrium.

54 Claims, 6 Drawing Sheets

(51) Int. Cl.
*A61M 60/178* (2021.01)
*A61M 60/216* (2021.01)
*A61M 60/422* (2021.01)
*A61M 60/538* (2021.01)
*A61M 60/569* (2021.01)
*A61M 60/81* (2021.01)
*A61M 60/861* (2021.01)

(52) U.S. Cl.
CPC ........ *A61M 60/422* (2021.01); *A61M 60/538* (2021.01); *A61M 60/569* (2021.01); *A61M 60/81* (2021.01); *A61M 60/861* (2021.01)

(56) References Cited

U.S. PATENT DOCUMENTS

| | | | |
|---|---|---|---|
| 5,092,879 A | | 3/1992 | Jarvik |
| 5,947,892 A | * | 9/1999 | Benkowski ......... A61M 60/806 |
| | | | 600/16 |
| 6,302,910 B1 | * | 10/2001 | Yamazaki ........... A61M 60/174 |
| | | | 623/3.13 |
| 6,858,001 B1 | * | 2/2005 | Aboul-Hosn ....... A61M 1/3653 |
| | | | 623/3.13 |
| 7,479,102 B2 | | 1/2009 | Jarvik |
| 9,636,441 B2 | | 2/2017 | Jarvik |
| 11,534,593 B2 | * | 12/2022 | Franano ............. A61M 60/232 |
| 2002/0026944 A1 | * | 3/2002 | Aboul-Hosn ....... A61M 60/411 |
| | | | 128/898 |
| 2017/0296723 A1 | | 10/2017 | Garrigue |
| 2018/0207336 A1 | * | 7/2018 | Solem ................ A61M 60/289 |
| 2018/0280668 A1 | * | 10/2018 | Alaswad ............ A61M 60/857 |
| 2021/0038791 A1 | * | 2/2021 | Tuval ................. A61M 60/812 |

OTHER PUBLICATIONS

Mitamura et al:, "The Valvo-Pump An Axial, Nonpulsatile Blood Pump," ASAIO Journal 37.3 (1991): p. M510-M512.
European Examination Report for corresponding Application No. 19 797 505.5-1113, dated Nov. 12, 2023 for applicant The Cleveland Clinic Foundation, pp. 1-7.

* cited by examiner

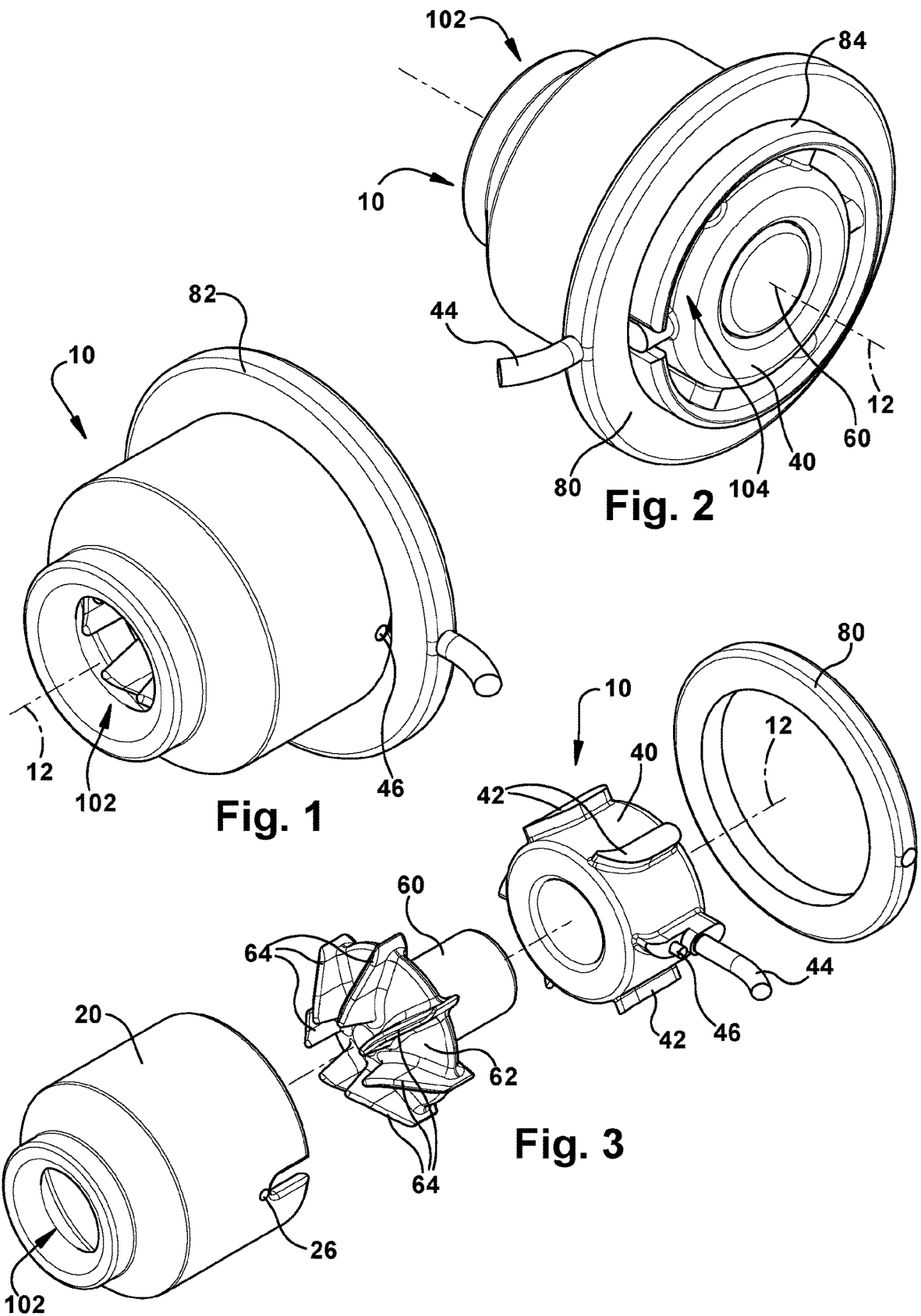

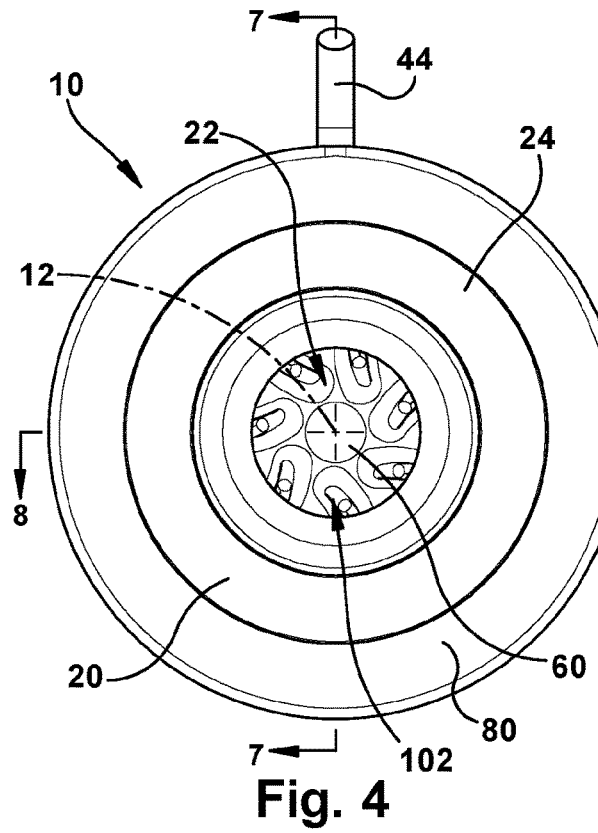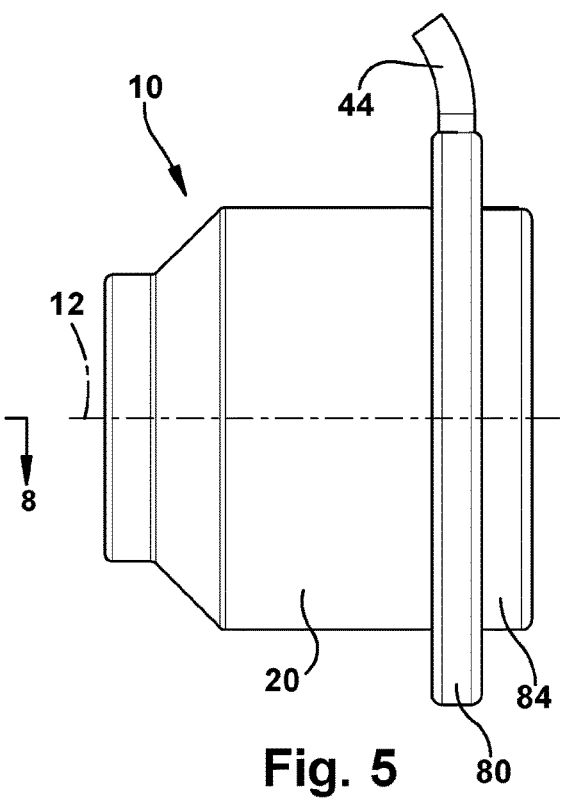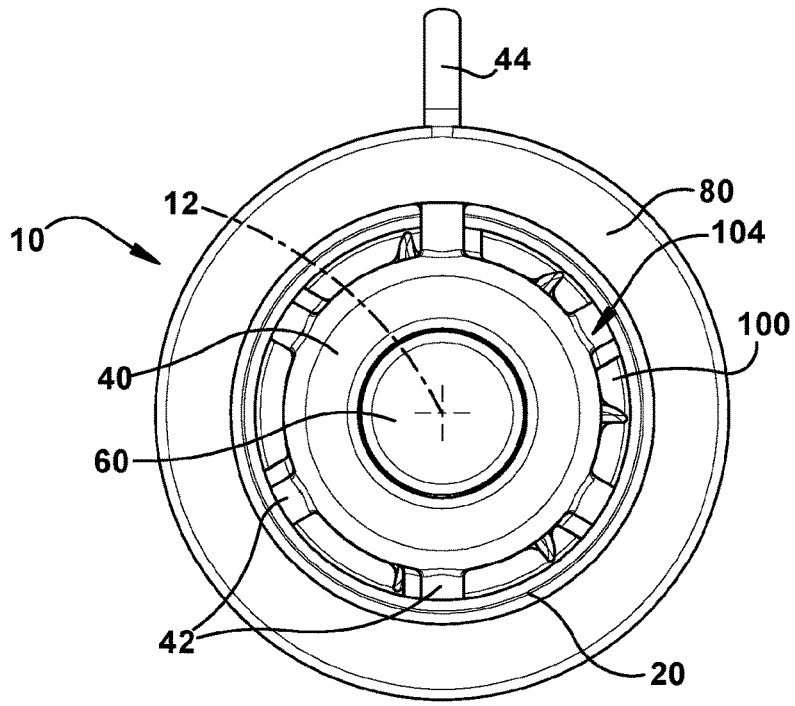

ATRIAL ASSIST DEVICE

RELATED APPLICATION

This application claims priority from U.S. Patent Application Ser. No. 62/745,588, filed Oct. 15, 2018, which is incorporated herein in its entirety.

BACKGROUND

Heart failure is a heterogeneous disease that can have a wide variety of indications. In some instances, the heart muscle contracts normally but the ventricles do not relax as they should during ventricular filling (or when the ventricles relax). For some patients, the heart muscle can become so thick and stiff that the ventricle holds a smaller-than-usual volume of blood, it might still seem to pump out a normal percentage of the blood that enters it, i.e., a normal ejection fraction. This condition is identified as heart failure with preserved ejection fraction (HFpEF). Even though the ejection fraction is normal or preserved, the total amount or volume of blood pumped by the heart isn't enough to meet the needs of the patient's body. For other patients, the ejection fraction is reduced. This condition is identified as heart failure with reduced ejection fraction (HFrEF). Accordingly, there is a need to address the ventricular filling issues associated with these and other types of heart failure.

Epidemiologic studies have shown that HFpEF comprises half of all heart failure cases. Compared to heart failure with reduced ejection fraction (HFrEF), the overall survival in HFpEF may be better, as suggested in a recent meta-analysis. Large community-based studies and studies in patients following hospitalization for heart failure have, however, reported similarly poor outcomes in HFpEF in terms of mortality and re-hospitalization rates. Yet, in sharp contrast to the wealth of proven therapies for HFrEF, trials of conventional heart failure medications have been inconclusive in HFpEF. To date, there is no therapy proven to reduce mortality in HFpEF. A greater understanding of the distinct pathophysiologic processes in HFpEF is key for the development of novel therapeutic approaches.

HFpEF is a common cause of complex pulmonary hypertension in the elderly. Elderly patients with pulmonary hypertension and normal LV chamber size and systolic function on transthoracic echocardiogram should be evaluated for HFpEF. Recent epidemiologic studies have established that the prevalence of HFpEF among patients with heart failure averages 54%, with a range from 40% to 71%. Its prevalence in the community is estimated to be 1.1% to 5.5% of the general population. The prevalence of HFpEF has increased over the last 2 decades, in association with an aging population and increasing prevalence of risk factors, such as hypertension and diabetes mellitus.

The diagnosis of HFpEF can be challenging since symptoms are nonspecific and signs may be absent or difficult to elucidate, particularly in the outpatient setting. A thorough evaluation is needed to diagnose the heart failure syndrome, since it is a strictly clinical diagnosis. It is important to exclude other conditions that may present in a similar manner.

The prevalence HFpEF continues to increase in the developed world, likely because of the increasing prevalence of common risk factors, including older age, female sex, hypertension, metabolic syndrome, renal dysfunction and obesity. Historically, HFpEF was termed diastolic heart failure. Recent investigations, however, suggest a more complex and heterogeneous pathophysiology. Ventricular diastolic and systolic reserve abnormalities, chronotropic incompetence, stiffening of ventricular tissue, atrial dysfunction, pulmonary hypertension, impaired vasodilation, and endothelial dysfunction are all implicated.

During diastole, normal ventricular filling is achieved when the ventricle relaxes and the ventricular pressure drops toward atmospheric, allowing the left atrial pressure, which can be aided by atrial contraction, to fill the ventricle. In patients with HFpEF, however, ventricular filling becomes dependent on high left atrial pressure to actively push blood into the left ventricle (LV), as opposed to the normal filling physiology. Passive LV end-diastolic stiffness (Eed) is quantified by the slope and position of the diastolic pressure-volume relationship. Eed increases with normal aging, but this increase is exaggerated in individuals with HFpEF in most, but not all studies.

Atrial fibrillation is extremely common in HFpEF (seen at some point in two-thirds of patients) and poorly tolerated because of the importance of left atrial contractile function in maintaining adequate LV chamber filling. The cardinal symptomatic manifestations of heart failure are dyspnea, fatigue, and exercise intolerance, regardless of ejection fraction. Despite similar symptoms, HFpEF patients differ from HFrEF in that they tend to be somewhat older and more likely to be female, obese, hypertensive, and in atrial fibrillation. In HFpEF, there is inability to enhance early diastolic relaxation and suction with exercise or tachycardia, contributing to increase filling pressures. There is also an increase in "passive" LV chamber stiffness in HFpEF, so that even if relaxation and suction were adequate, a higher filling pressure would be required to distend the chamber to an adequate preload volume.

Approximately 50-60% of patients with heart failure have HFpEF, and its prevalence is increasing. HFpEF is a systemic syndrome that goes far beyond diastolic dysfunction, however, it is typically associated with an increase in LV diastolic pressure through abnormalities in diastolic function, specifically related to impaired relaxation and stiffness.

SUMMARY

An atrial assist device assists the blood pumping function of the native heart. In one configuration, the assist device pumps blood from a low pressure cardiac chamber (atrium) into high pressure cardiac chamber (ventricle). The assist device can deliver blood into a failed ventricle, not into the systemic (body) or pulmonary (lungs) circulation. The blood is directly delivered from the atrial chamber into the ventricle. The atrial assist device enables native heart to be filled properly, as opposed to other devices that empty the ventricle and pump blood into circulation (systemic or pulmonary). The atrial assist device helps the native ventricle pump blood into systemic and/or pulmonary circulation, which provides physiological pressure and flow waveforms. This is opposed to pumps that bypass or otherwise exclude the ventricle from participating in ejection, which alters the pulsatility of blood flow and undermines the recovery of the ventricle. The atrial assist device therefore increases the blood volume in the ventricle prior to the ejection phase vs. decreasing the blood volume with other blood pump technologies. This renders the atrial assist device effective in achieving treatment goals of reducing left or right atrial pressure and increasing cardiac output for diseases when ventricular diastolic (filling) is damaged, and ventricular systolic (ejecting) function is preserved.

According to one aspect, a system for treating a patient with a heart condition includes an atrial assist device (AAD)

configured to be positioned in the patient's heart to pump blood from an atrium of the patient's heart into a ventricle associated with the atrium. The system also includes a controller operatively connected to the AAD and being configured to control the AAD to pump blood from the atrium of the patient's heart into the ventricle associated with the atrium.

According to another aspect, alone or in combination with any other aspect, the controller can be configured to control the AAD to assist with the filling of the ventricle during the normal cardiac cycle of the heart.

According to another aspect, alone or in combination with any other aspect, controlling the AAD to assist with the filling of the ventricle during the cardiac cycle of the heart can include modulating the electrical current supplied to the AAD and synchronizing the current modulation to coincide with diastole and systole phases of the cardiac cycle of the heart.

According to another aspect, alone or in combination with any other aspect, modulating the electrical current supplied to the AAD can include modulating the electrical current supplies to the ADD between a first current and second current, wherein the second current is greater than the first current. Synchronizing the current modulation to coincide with diastole and systole phases of the cardiac cycle of the heart can include supplying the first current to the AAD at least partially in synchronization with a diastole phase of the cardiac cycle of the patient's heart, and supplying the second current to the AAD at least partially in synchronization with a diastole phase of the cardiac cycle of the patient's heart.

According to another aspect, alone or in combination with any other aspect, supplying the first current to the AAD can include supplying the first current to the AAD for a duration defined by a myocardial perfusion time. The myocardial perfusion time can be a time period determined to be sufficient to allow for myocardial perfusion during diastole. Supplying the second current to the AAD can include supplying the second current to the AAD at all times other than those when the first current is supplied to the AAD.

According to another aspect, alone or in combination with any other aspect, the myocardial perfusion time can be of a duration that is less than or equal to the duration of the diastole phase of the cardiac cycle of the patient's heart.

According to another aspect, alone or in combination with any other aspect, supplying the first current to the AAD can include detecting the onset of diastole and supplying the first current to the AAD in response to detecting the onset of diastole for the duration defined by the myocardial perfusion time.

According to another aspect, alone or in combination with any other aspect, detecting the onset of diastole can include monitoring pump speed and inferring diastole in response to an increase in the monitored pump speed.

According to another aspect, alone or in combination with any other aspect, the second current can be configured to cause the AAD to accelerate in speed to prevent backflow into the atrium during systole.

According to another aspect, alone or in combination with any other aspect, the controller can be configured to operate the AAD to pump blood from the ventricle through a mitral valve of the patient's heart into the ventricle, and to permit the mitral valve to close to prevent backflow into the atrium during systole.

According to another aspect, alone or in combination with any other aspect, the heart condition can be heart failure.

According to another aspect, alone or in combination with any other aspect, the atrium can be the left atrium and the ventricle can be the left ventricle.

According to another aspect, alone or in combination with any other aspect, the AAD can be configured to be positioned in a mitral valve position.

According to another aspect, alone or in combination with any other aspect, the system can include a sewing cuff for suturing the AAD in the mitral valve position after at least a portion of the mitral valve has been surgically excised.

According to another aspect, alone or in combination with any other aspect, the AAD can be configured to be connected to an annular portion of the mitral valve after a portion of the mitral valve has been surgically excised.

According to another aspect, alone or in combination with any other aspect, the system can include a sewing cuff for suturing the AAD to the mitral valve.

According to another aspect, alone or in combination with any other aspect, the AAD can be configured to be positioned in the atrium on top of the mitral valve.

According to another aspect, alone or in combination with any other aspect, the AAD can be configured to allow the mitral valve and sub-valvular structures to remain in place.

According to another aspect, alone or in combination with any other aspect, the system can include a sewing cuff for suturing the AAD to heart structures surrounding mitral valve.

According to another aspect, a method for treating a patient with a heart condition includes positioning an atrial assist device (AAD) in the patient's heart, and operating the AAD to pump blood from an atrium of the patient's heart into a ventricle associated with the atrium.

According to another aspect, alone or in combination with any other aspect, operating the AAD can include controlling the AAD to assist with the filling of the ventricle during the normal cardiac cycle of the heart.

According to another aspect, alone or in combination with any other aspect, controlling the AAD to assist with the filling of the ventricle during the cardiac cycle of the heart can include modulating the electrical current supplied to the AAD and synchronizing the current modulation to coincide with diastole and systole phases of the cardiac cycle of the heart.

According to another aspect, alone or in combination with any other aspect, modulating the electrical current supplied to the AAD can include modulating the electrical current supplies to the ADD between a first current and second current, wherein the second current is greater than the first current. Synchronizing the current modulation to coincide with diastole and systole phases of the cardiac cycle of the heart can include supplying the first current to the AAD at least partially in synchronization with a diastole phase of the cardiac cycle of the patient's heart, and supplying the second current to the AAD at least partially in synchronization with a diastole phase of the cardiac cycle of the patient's heart.

According to another aspect, alone or in combination with any other aspect, supplying the first current to the AAD can include supplying the first current to the AAD for a duration defined by a myocardial perfusion time, the myocardial perfusion time being a time period determined to be sufficient to allow for myocardial perfusion during diastole. Supplying the second current to the AAD can include supplying the second current to the AAD at all times other than those when the first current is supplied to the AAD.

According to another aspect, alone or in combination with any other aspect, the myocardial perfusion time can be of a duration that is less than or equal to the duration of the diastole phase of the cardiac cycle of the patient's heart.

According to another aspect, alone or in combination with any other aspect, supplying the first current to the AAD can include detecting the onset of diastole and supplying the first current to the AAD in response to detecting the onset of diastole for the duration defined by the myocardial perfusion time.

According to another aspect, alone or in combination with any other aspect, detecting the onset of diastole can include monitoring pump speed and inferring diastole in response to an increase in the monitored pump speed.

According to another aspect, alone or in combination with any other aspect, the second current can be configured to cause the AAD to accelerate in speed to prevent backflow into the atrium during systole.

According to other aspects, alone or in combination with any other aspect(s), positioning the AAD further can include positioning the AAD in the mitral valve position. Positioning the AAD can include excising at least a portion of the mitral valve and suturing the AAD in the mitral valve position using a sewing cuff. Positioning the AAD can include excising a portion of the mitral valve, leaving an annular portion of the mitral valve intact, and connecting the AAD to the annular portion of the mitral valve. Positioning the AAD can include suturing the AAD to the mitral valve using a sewing cuff. Positioning the AAD can include positioning the AAD on top of the mitral valve. Positioning the AAD can include allowing the mitral valve and subvalvular structures to remain in place. Positioning the AAD can include suturing the AAD to heart structures surrounding mitral valve using a sewing cuff.

According to another aspect, alone or in combination with any other aspect, operating the AAD can include pumping blood through the mitral valve into the ventricle, and permitting the mitral valve to close to prevent backflow into the atrium during systole.

DRAWINGS

FIG. 1 is a front perspective view of an atrial assist device (AAD) according to an example configuration of the invention.

FIG. 2 is a rear perspective view of the AAD.

FIG. 3 is an exploded perspective view of the AAD.

FIG. 4 is front view of the AAD.

FIG. 5 side view of the AAD.

FIG. 6 is a rear view of the AAD.

Figure 7:
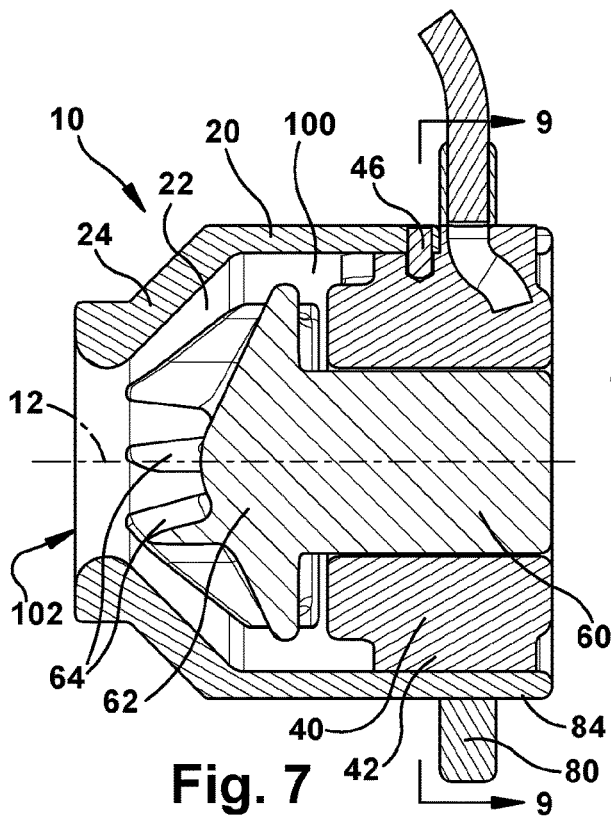

FIG. 7 is a section view taken generally along line 7-7 in FIG. 4.

Figure 8:
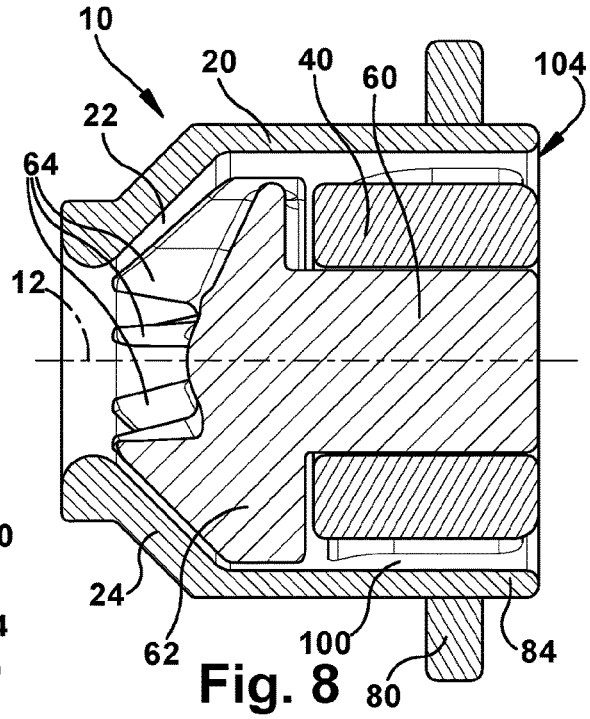

FIG. 8 is a section view taken generally along line 8-8 in FIG. 4.

Figure 9:
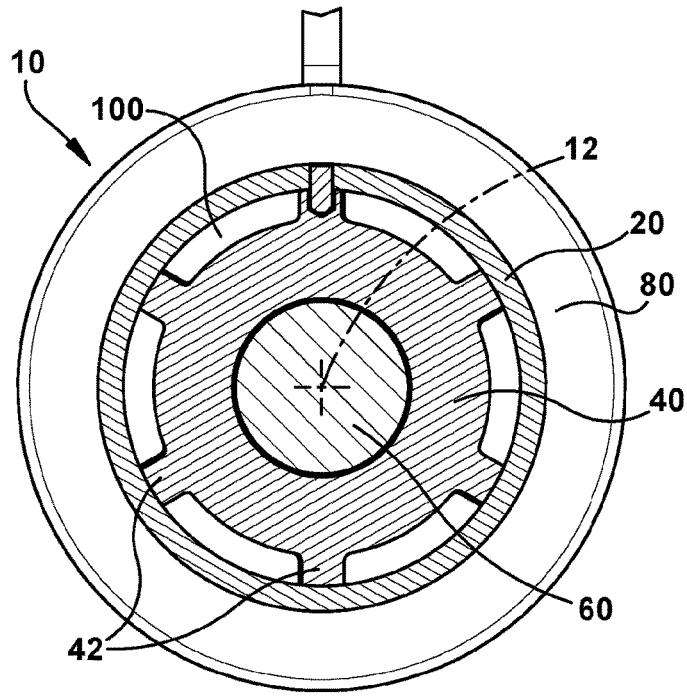

FIG. 9 is a section view taken generally along line 9-9 in FIG. 7.

Figure 10A:
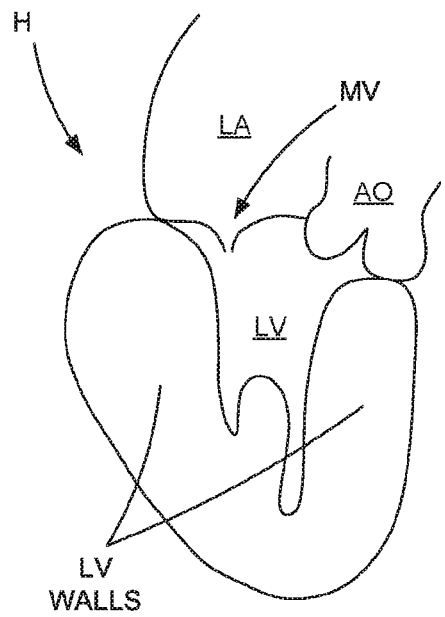

FIG. 10A is a schematic illustration of a heart experiencing heart failure.

Figure 10B:
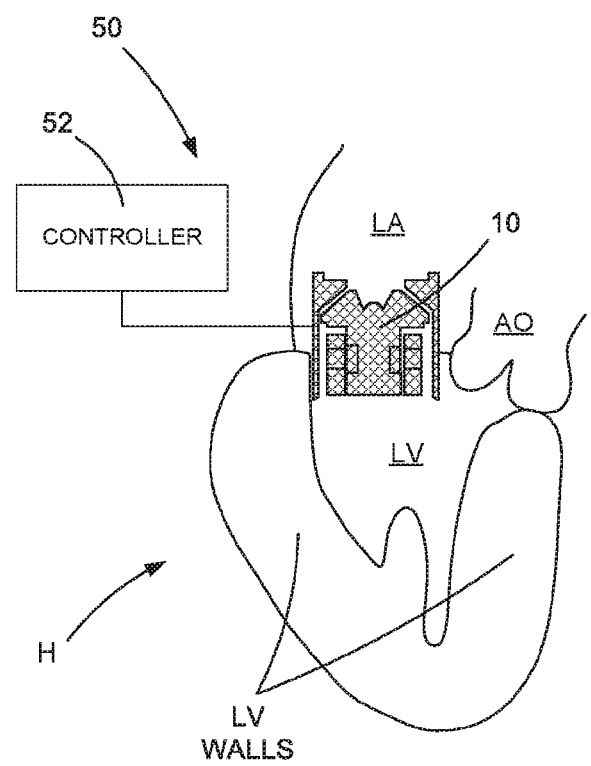

FIG. 10B is a schematic illustration depicting the AAD in a first surgical placement in the heart.

Figure 11:
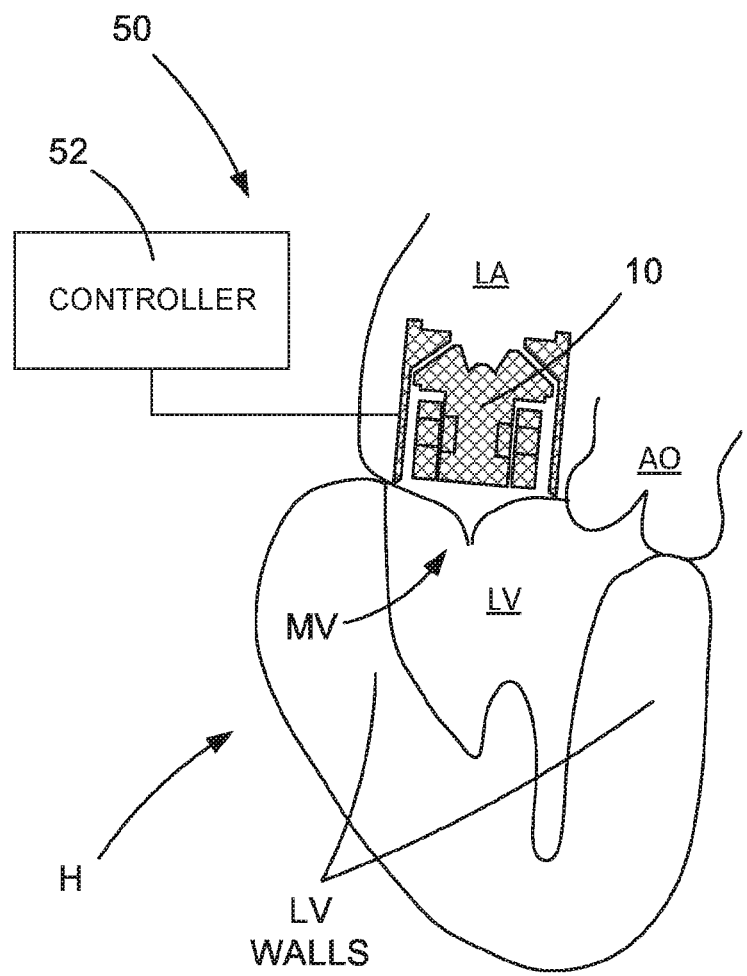

FIG. 11 is a schematic illustration depicting the AAD in a second surgical placement in the heart.

Figure 12:
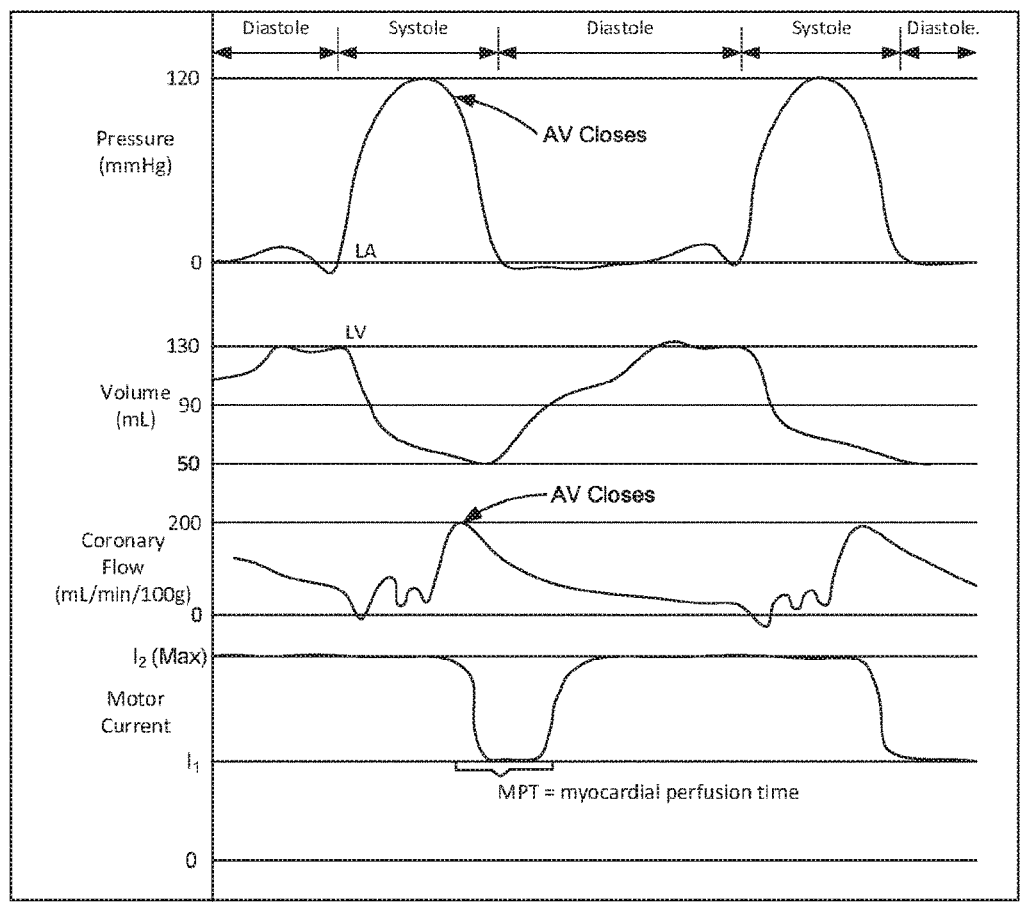

FIG. 12 is a chart illustrating a control scheme for controlling the operation of the AAD.

DESCRIPTION

Improvements in the condition of patients with heart failure can be achieved through addressing the filling of the LV. The present invention is a system and method for implementing a therapy for heart failure. In patients with LV stiffness, the LV cavity is small due to thickened and stiffened LV muscle (impaired compliance). The left atrium (LA) is usually dilated and LA pressure (LAP) is elevated because it requires much force (pressure) for the LA to pump blood to the stiffened LV. Dilatation of the LV cavity and improvement of the LV compliance will be the primary therapy for this physiology, but it's not very easy to achieve it.

Referring to FIGS. 10-11, the system 50 includes an atrial assist device (AAD) 10 and a controller 52 for controlling operation of the AAD. The system 50 can be implemented to assist the native heart in moving blood from the atrium into the ventricle on either side, i.e., the left or right side, of the heart. In this description, the AAD 10 is described in a left side implementation, i.e., a LAAD, because this is where the perceived need is most prevalent. It should be understood, however, that the AAD 10 is suitable for either left side or right side implementation, so the assist device is referred to as an AAD. The system 50 implementing the AAD 10 will provide the volume filling and adequate pressurization of the LV required to trigger natural mechanisms of blood ejection.

According to the method of the invention, the AAD 10 is implemented as a left atrial assist device (LAAD) positioned at the mitral valve (MV) position of the heart H to pump blood from the LA to the LV, thus reducing LAP and increasing LV volume. Cardiac output should increase when the LV volume increases. The controller 52 can operate the AAD 10 using constant or modulated control based, for example, on speed, power, or current, all of which are related pump operating characteristics.

With the AAD 10 operating at a constant speed, the pump flow is higher and pressure is lower during diastole due to a low LVP-LAP pressure differential. Conversely, the pump flow is lower and pressure is higher during systole due to a higher LVP-LAP pressure differential. Constant speed, however, can result in increased LVP throughout the cardiac cycle. Because of this, it can be desirable to modulate operation of the AAD 10 in order to control ventricular pressure. This is because maintaining high ventricular pressure (LVP) throughout the cardiac cycle can prevent myocardial perfusion, which can lead to heart stoppage. The AAD modulation can therefore be implemented to cycle the LVP in order to myocardial perfusion while at the same time maintaining flow sufficient to prevent backflow through the pump during systole.

As a result of implementing the system 50, the assist delivered to the native pumping of the LV will, over time, result in enlargement and remodeling the LV anatomy and structure, which changes the compliance of the heart muscle. As this remodeling evolves and the heart muscle becomes more compliant, the amount of assist required by the patient's heart will be reduced. As a result, the AAD pump speed can be reduced over time, based on improvements in the LVP and/or physiologic state of the patient. The AAD could even be removed if the LV function improves to a self-sustaining level.

It is important to note that the system 50 doesn't necessarily alter the normal cardiac physiology mechanism or natural blood flow direction. Advantageously, rather than simply pumping the blood from the LA to the AO, this method maintains the desired blood flow path from the LA to the LV to the AO. Pulsatility can also be adjusted to optimal degrees and maintained due to the beating of the native heart in combination with the modulated pump control. Because of this, a normal blood flow pattern, in terms of flow rates and pressures, can be maintained. This provides a better potential for healing the failing heart through anatomical and structural remodeling.

Conventional ventricular assist pump wisdom is directed toward providing adequate blood flow without concern for maintaining the natural blood flow path. The conventional systems implement pumps located, in whole or in part, external to the heart, which bypass the LV partially or completely, with the sole intent being to maintain blood flow to the AO. These conventional systems and methods fail to appreciate the potential for healing the failing heart through the remodeling achieved by directing all blood flow through the natural blood flow path.

In-the-Valve Mitral Valve Pump Position

The system 50 and method of the invention can be designed for positioning the AAD 10 in the heart or external to the heart. An example implementation of the system 50 and method in which the AAD 10 is positioned for in the heart is shown in FIGS. 10A and 10B. In this example implementation, the AAD 10 is positioned in the mitral valve (MV) position in the heart (H).

In FIG. 10A, the heart H with heart failure has thick LV walls, which result in a small LV volume. In FIG. 10B, the AAD 10 is positioned in the mitral valve MV position, which allows the pump to draw blood in from the left atrium LA and discharge blood into the left ventricle LV while the heart H continues to function and beat. The AAD 10 increases the flow into the LV, which causes the blood volume of each ejection to increase. This increased blood volume causes the LV itself to increase in volume, i.e., causes remodeling of the LV walls, which become thinner and more compliant. Over time, as the LV walls thin, the patient can be weened from the pump, the heart failure condition having been remedied.

On-the-Valve Mitral Valve Implantation

An example implementation of the system 50 and method of the invention in which the AAD 10 is positioned on top of the mitral valve MV is shown in FIG. 11. According to this system configuration/implantation method, the AAD 10 is still positioned at the MV annulus but the entire pump body is in the left atrium LA. This eliminates, in part or in full, the need to remove the MV and allows the MV to function to prevent potential regurgitation/backflow during diastole. This can reduce or eliminate the need to utilize high pump speeds to overcome regurgitation where the MV is replaced by the AAD 10, such as the in-the-valve implantation described above. As a result, for this configuration, the overall height can be reduced because the larger motor height needed to produce higher speeds will not be needed.

As a further optional configuration, the AAD 10 of FIG. 10A could itself be outfitted with an artificial, mechanical mitral valve replacement at the outflow of the pump. This valve would prevent the aforementioned regurgitation/backflow, thereby eliminating the need to cycle pump speed.

Surgical Embodiment

An example configuration of an AAD 10 that can be implemented in the system 50 and used to implement the methods described herein is illustrated in FIGS. 1-9. As shown in FIGS. 1-9, the AAD 10 includes an outer housing 20 with a sewing cuff 80 that permits the device to be sewn into position in the heart. In the LAAD implementation, the cuff 80 would facilitate sewing the AAD 10 to the heart in the mitral valve position. The mitral valve can be excised and the AAD 10 can be sewn in its place (FIG. 10B) or the mitral valve can be left in place and the AAD can be sewn on top of it (FIG. 11). Alternatively, for the in-the-valve implantation (FIG. 10B), a portion of the mitral valve can be left intact and the pump can be sutured or affixed to the device landing zone within or in proximity to the native atrio-ventricular groove. When the AAD 10 is removed post-therapy, the remainder of the valve can be removed and replaced with a prosthetic replacement valve.

The shape of the housing 20 and of the AAD 10 illustrated in FIGS. 1-9 is by way of example only. The shape of the AAD 10, particularly the housing 20, can be configured based on a variety of factors. For example, the shape of the housing 20 can be dictated or influenced by the anatomy at which the pump is positioned, e.g., on-the-valve or in-the-valve (see above). As another example, the shape of the housing 20 can be dictated or influenced by the desired degree of pumping performance, e.g., LV assist vs. RV assist. As a futher example, the shape of the housing 20 can be dictated or influenced by structural or performance requirements, such as the stability with which the pump is anchored to the heart tissue. In this respect, for example, the housing 20 could be tapered or funnel-shaped so that the houisng walls rest on the tissue adjacent the AAD 10. The shape of the cuff 80, the number of cuffs, and the position of the cuff on the housing 20 can also be configured to meet these structureal and performance requirements.

A stator 40 and rotating assembly or rotor 60 are supported in the housing 20. The rotor 60 is received in the stator 40 and the stator is retained in the housing, for example, via a shrink fit or interference fit that is held in place by a retainer 46, such as a pin or set screw, that engages an opening 26 in the housing 20. In the assembled condition, the stator 40 and rotor 60 are centered along an axis 12 of the AAD 10.

The rotor 60 includes an impeller 62 that includes a plurality of vanes 64. The impeller 62 is supported in a portion of the housing 20 that defines a pumping chamber 22. In the example configuration shown in the figures, the pumping chamber has a generally frusto-conical configuration with a conically tapered sidewall 24 that converges and terminates at the pump inlet 102. The rotor 60 is rotatable relative to the stator 40 about the axis 12 of the AAD 10 to move pumped fluid, i.e., blood, from the pump inlet 102 to a pump outlet 104.

The stator 40 is supported centrally by stator supports 42 that space the stator from the housing wall to define an annular flow channel 100. The flow channel 100 extends from the pump inlet 102 to the pump outlet 104. The stator supports 42 are positioned in the flow channel 100. In addition to supporting the stator 40, the stator supports 42 can also serve as flow stratghtening vanes and can have a curved configuration arranged to oppose the direction of swirl induced in the pumped blood by the rotation of the rotor 60.

The stator 40 includes stator windings that are electrically connected to a cable 44. The cable 44 extends externally of the housing 20 and can extend externally of the patient to a pump controller that can supply power to the AAD 10 and can communicate with the AAD. The rotor 60 includes a permanent magnet assembly. To operate the AAD 10, the controller excites the stator coils to produce a rotating electromagnetic field that induces rotation of the rotor 60 in a known manner. The AAD 10 pumps blood from the inlet 102 to the outlet 104.

Attachment—Sewing Cuff

In the configuration of the AAD 10 illustrated in FIGS. 1-9, a sewing cuff 80 is secured to the outer surface of the housing 20. The sewing cuff 80 protrudes radially outward of the outside diameter of the housing 20 and allows the cable 40 to pass through radially outward, so as to reduce its exposure to blood in the heart. In this example configuration, the sewing cuff 80 facilitates connecting the AAD 10 to the patient's heart tissue during implantation. In the example configuration of FIGS. 1-9, the sewing cuff 80 is formed at a proximal end 84 of the AAD 10, adjacent the pump outlet 104. The sewing cuff 80 could have other locations, such as a central location on the pump housing 20.

The sewing cuff 80 can, for example, be formed as a portion of the housing 20 or can be formed as a separate structure secured to the housing. The sewing cuff 80 is at least partially constructed of a material that facilitates sewing to the native heart structure, e.g., via suture. The sewing cuff 80 can, for example be at least partially constructed of a fabric, such as polyester, e.g., Dacron® (a long chain polyester made from ethylene glycol and terephthalic acid), Teflon® (a polytetrafluoroethylene (PTFE) polymer material), or a combination thereof.

The sewing cuff 80 can have a variety of configurations. For example, the sewing cuff 80 can include one or more inner rings or wires covered by a cloth or fabric material (e.g., Dacron® or Teflon®) The sewing cuff 80 can be fitted onto the AAD 10, e.g., onto the housing 20, with the ring(s)/wire(s) engaging the structure to secure the sewing cuff 80 in place. To facilitate this connection, the structure to which the sewing cuff 80 is secured, e.g., the housing 20, can include an annular recess for receiving the ring(s)/wire(s) and thereby connecting the fabric/cloth to the AAD 10.

In one particular configuration, the sewing cuff 80 can be a standard, conventional sewing cuff, such as those used in mitral valve replacement surgery. Instead of being used to support the replacement valve, the sewing cuff 80 supports the AAD 10. To achieve this, the AAD 10 can be configured to cooperate with the sewing cuff 80 so that the cuff can support the AAD. For example, the AAD 10 can include a cuff receiving groove formed on the outer surface of the pump housing 20. The cuff 80 can be received in the groove to secure the cuff to the AAD 10. As another example, the conventional sewing cuff 80 can be secured to the housing 20 via clamp.

The sewing cuff 80 facilitates sewing the AAD 10 to the heart via sutures. The sewing cuff 80 can be sewed to the periphery or annulus of the annular heart valve body, e.g., the mitral valve in the case of an HFpEF patient, to anchor the AAD 10. Although a single sewing cuff 80 is illustrated, the AAD 10 could include two or more sewing cuffs to provide a more robust securement and to accommodate the cyclical movement of the pump during normal operation.

AAD Pump Operation

During operation of the AAD 10, as the rotor 60 rotates, the impeller 60 draws an inflow of blood from the artium axially into the pumping chamber 22 through the inlet 102. The blood passes over/through the impeller vanes and is directed though flow channel 100, where the stator supports 42 straighten the blood flow so as to be more axially oriented. The blood is discharged from the AAD 10 through the outlet 104 into the ventricle.

As can be seen, structurally, the native heart chamber, i.e., the atrium, acts as the inflow for the AAD 10 and may have a role in forming the blood flow pattern and flow stabilization in accordance with device placement site. Because of this, the AAD 10 has a somewhat unique profile: short, so as not to interfere with the atrium walls, and having a width to occupy or substantially occupy the comparatively wide mitral valve opening. Because of its placement in the mitral valve position, the AAD 10 tends to move up and down with the native heart pumping action. Additionally, the pump can undergo rotational torques during periods of acceleration, such as when the pump speed is modulated. Therefore, this short and wide configuration may be advantageous in terms of resisting these movements and mitigating their effects. In one configuration, the AAD 10 can have a diameter of about 30 mm, and a height of about 30 mm.

Because the AAD 10 is positioned in the atrium, especially for the on-the-valve mitral valve AAD placement, the inlet can be positioned in somewhat close proximity to in the structures of the atrium, which can lead to concerns over tissue suction at the pump inlet. The atrium can be somewhat enlarged in heart failure patients so, initially, this is not a great concern. As the heart heals, however, the atrium returns to normal size, so inlet suction becomes more of a concern. For this reason, the AAD 10 can include an inlet cage and/or an outlet cage that covers the inlet and prevents tissue from getting sucked in.

LAAD Control Algorithm

The system 50 implements a control algorithm, programmed in the controller 52, which is used to control operation of the AAD 10 in an LAAD implementation. The control algorithm implements a current control mode on the motor, as opposed to speed control, to avoid high left ventricular diastolic pressure and to provide sufficient myocardial perfusion during operation of the AAD 10. Referring to FIG. 12, there are three parameters that the controller 52 can adjust or change to implement this pump control algorithm: $I_1$, $I_2$, and MPT. $I_1$ is a lower current, $I_2$ is a higher current, and MPT is the myocardial perfusion time, which is the amount of time (or the percentage of the cardiac cycle) that the controller 52 runs the AAD 10 at $I_1$. $I_1$ is used to reduce ventricular pressure and allow for perfusion of the myocardium. $I_1$, $I_2$, and MPT are tunable parameters that can be adjusted by the clinician. Additional currents between $I_1$ and $I_2$, e.g., $I_3$, and corresponding perfusion times/cardiac cycle percentages, can also be implemented and/or tuned.

Assuming that no mitral valve is in place (see, FIG. 10B), 12 is chosen/tuned to be high enough to stop regurgitant flow, and to hit the cardiac output target set by the clinician. $I_1$ is chosen/tuned such that there is positive forward flow at the start of diastole, but the left ventricular pressure remains low enough that myocardial perfusion is good, and also low enough that the inlet does not get into a suction condition. The duration of MPT is chosen/tuned so that it is long enough to get the myocardial perfusion needed, but short enough to get the desired cardiac output given that there are limits to how high $I_2$ can be.

The reason that the control algorithm modulates motor current between two values is that there is no reason for the AAD 10 to pump at a power lower than necessary for a given cardiac output except during the time period when the myocardium is being perfused. By setting the $I_1$ current at a low value, which produces low torque and low power, it will ensure that the LV will not be compressed during the MPT and myocardium perfusion will take place. As soon as MPT expires, however, the AAD 10 should pump at an increased power that will generate the desired cardiac output, regardless of the pressure rise of the AAD.

During operation, the controller 50 needs to sync the current supplied to the AAD 10 with the cardiac cycle of the heart H. Because the AAD 10 is operated using the current control mode, the speed at any given time will be a function of flow and pressure rise across the pump and therefore may have an unusual shape. Monitoring the pump speed can allow for detecting the aortic valve closure, and this can be used as a trigger to start the MPT and change the control current to $I_1$. At the minimum, the pump speed can be monitored to determine when the pressure rise across the pump peaks. The occurrence of peak pump pressure rise can trigger the start of the MPT and change the control current to $I_1$.

What have been described above are example configurations of the invention. Those having ordinary skill in the art will appreciate that the systems, devices, and methods described herein can be altered or modified to produce different variations without departing from the spirit and scope of the invention. This disclosure is intended to embrace any and all such alterations, modifications, and variations that fall within the scope of this application, including the appended claims.

We claim:

1. A system for treating a patient with a heart condition, comprising:
   an atrial assist device (AAD) configured to be positioned in an atrium of the patient's heart to pump blood from the atrium into a ventricle associated with the atrium to assist in filling the ventricle with blood; and
   a controller operatively connected to the AAD and being configured to control the AAD to pump blood from the atrium of the patient's heart into the ventricle, wherein the controller is configured to control the AAD to assist with the filling of the ventricle during the normal cardiac cycle of the heart by modulating the electrical current supplied to the AAD and synchronizing the current modulation to coincide with diastole and systole phases of the cardiac cycle of the heart, wherein:
   modulating the electrical current supplied to the AAD comprises modulating the electrical current supplies to the ADD between a first current and second current, wherein the second current is greater than the first current; and
   synchronizing the current modulation to coincide with diastole and systole phases of the cardiac cycle of the heart comprises:
   supplying the first current to the AAD at least partially in synchronization with a diastole phase of the cardiac cycle of the patient's heart; and
   supplying the second current to the AAD at least partially in synchronization with a diastole phase of the cardiac cycle of the patient's heart.

2. The system recited in claim 1, wherein:
   supplying the first current to the AAD comprises supplying the first current to the AAD for a duration defined by a myocardial perfusion time, the myocardial perfusion time being a time period determined to be sufficient to allow for myocardial perfusion during diastole; and
   supplying the second current to the AAD comprises supplying the second current to the AAD at all times other than those when the first current is supplied to the AAD.

3. The system recited in claim 2, wherein the myocardial perfusion time is of a duration that is less than or equal to the duration of the diastole phase of the cardiac cycle of the patient's heart.

4. The system recited in claim 2, wherein supplying the first current to the AAD comprises detecting the onset of diastole and supplying the first current to the AAD in response to detecting the onset of diastole for the duration defined by the myocardial perfusion time.

5. The system recited in claim 4, wherein detecting the onset of diastole comprises monitoring pump speed and inferring diastole in response to an increase in the monitored pump speed.

6. The system recited in claim 1, wherein the second current is configured to cause the AAD to accelerate in speed to prevent backflow into the atrium during systole.

7. The system recited in claim 1, wherein the controller is configured to operate the AAD to pump blood from the atrium through a mitral valve of the patient's heart into the ventricle, and to permit the mitral valve to close to prevent backflow into the atrium during systole.

8. The system recited in claim 1, wherein the heart condition is heart failure.

9. The system recited in claim 1, wherein the atrium is the left atrium and the ventricle is the left ventricle.

10. The system recited in claim 9, wherein the AAD is configured to be positioned in a mitral valve position.

11. The system recited in claim 10, further comprising a sewing cuff for suturing the AAD in the mitral valve position after at least a portion of the mitral valve has been surgically excised.

12. The system recited in claim 9, wherein the AAD is configured to be connected to an annular portion of the mitral valve after a portion of the mitral valve has been surgically excised.

13. The system recited in claim 9, further comprising a sewing cuff for suturing the AAD to the mitral valve.

14. The system recited in claim 9, wherein the AAD is configured to be positioned in the atrium on top of the mitral valve.

15. The system recited in claim 14, wherein the AAD is configured to allow the mitral valve and sub-valvular structures to remain in place.

16. The system recited in claim 14, further comprising a sewing cuff for suturing the AAD to heart structures surrounding mitral valve.

17. The system recited in claim 1, wherein the AAD has an inlet configured to be positioned in the atrium and an outlet configured to discharge blood through a native heart valve into the ventricle.

18. The system recited in claim 17, wherein the outlet is configured to be positioned outside the atrium.

19. A system for treating a patient with a heart condition, comprising:
   an atrial assist device (AAD) configured to be positioned in the patient's heart to pump blood from an atrium of the patient's heart into a ventricle associated with the atrium; and
   a controller operatively connected to the AAD and being configured to control the AAD to pump blood from the atrium of the patient's heart into the ventricle associated with the atrium by modulating electrical current supplied to the AAD with a first current and a second current that is greater than the first current in synchronization with the cardiac cycle of the heart so that first current is supplied to the AAD during diastole to permit myocardial perfusion.

20. A system for treating a patient with a heart condition, comprising:
an atrial assist device (AAD) configured to be positioned in the patient's heart to pump blood from an atrium of the patient's heart into a ventricle associated with the atrium; and
a controller operatively connected to the AAD and being configured to control the AAD to pump blood from the atrium of the patient's heart into the ventricle associated with the atrium by modulating electrical current supplied to the AAD with a first current and a second current that is greater than the first current, wherein the controller is configured to supply the second current to the AAD in synchronization with systole to cause the AAD to accelerate in speed to prevent backflow into the atrium during systole.

21. The system recited in claim 19, wherein:
supplying the first current to the AAD comprises supplying the first current to the AAD for a duration defined by a myocardial perfusion time, the myocardial perfusion time being a time period determined to be sufficient to allow for myocardial perfusion during diastole; and
supplying the second current to the AAD comprises supplying the second current to the AAD at all times other than those when the first current is supplied to the AAD.

22. The system recited in claim 21, wherein the myocardial perfusion time is of a duration that is less than or equal to the duration of the diastole phase of the cardiac cycle of the patient's heart.

23. The system recited in claim 21, wherein supplying the first current to the AAD comprises detecting the onset of diastole and supplying the first current to the AAD in response to detecting the onset of diastole for the duration defined by the myocardial perfusion time.

24. The system recited in claim 23, wherein detecting the onset of diastole comprises monitoring pump speed and inferring diastole in response to an increase in the monitored pump speed.

25. The system recited in claim 19, wherein the second current is configured to cause the AAD to accelerate in speed to prevent backflow into the atrium during systole.

26. The system recited in claim 19, wherein the controller is configured to operate the AAD to pump blood from the atrium through a mitral valve of the patient's heart into the ventricle, and to permit the mitral valve to close to prevent backflow into the atrium during systole.

27. The system recited in claim 19, wherein the heart condition is heart failure.

28. The system recited in claim 19, wherein the atrium is the left atrium and the ventricle is the left ventricle.

29. The system recited in claim 28, wherein the AAD is configured to be positioned in a mitral valve position.

30. The system recited in claim 29, further comprising a sewing cuff for suturing the AAD in the mitral valve position after at least a portion of the mitral valve has been surgically excised.

31. The system recited in claim 28, wherein the AAD is configured to be connected to an annular portion of the mitral valve after a portion of the mitral valve has been surgically excised.

32. The system recited in claim 28, further comprising a sewing cuff for suturing the AAD to the mitral valve.

33. The system recited in claim 28, wherein the AAD is configured to be positioned in the atrium on top of the mitral valve.

34. The system recited in claim 33, wherein the AAD is configured to allow the mitral valve and sub-valvular structures to remain in place.

35. The system recited in claim 33, further comprising a sewing cuff for suturing the AAD to heart structures surrounding mitral valve.

36. The system recited in claim 19, wherein the AAD has an inlet configured to be positioned in the atrium and an outlet configured to discharge blood through a native heart valve into the ventricle.

37. The system recited in claim 36, wherein the outlet is configured to be positioned outside the atrium.

38. The system recited in claim 20, wherein:
supplying the first current to the AAD comprises supplying the first current to the AAD for a duration defined by a myocardial perfusion time, the myocardial perfusion time being a time period determined to be sufficient to allow for myocardial perfusion during diastole; and
supplying the second current to the AAD comprises supplying the second current to the AAD at all times other than those when the first current is supplied to the AAD.

39. The system recited in claim 38, wherein the myocardial perfusion time is of a duration that is less than or equal to the duration of the diastole phase of the cardiac cycle of the patient's heart.

40. The system recited in claim 38, wherein supplying the first current to the AAD comprises detecting the onset of diastole and supplying the first current to the AAD in response to detecting the onset of diastole for the duration defined by the myocardial perfusion time.

41. The system recited in claim 40, wherein detecting the onset of diastole comprises monitoring pump speed and inferring diastole in response to an increase in the monitored pump speed.

42. The system recited in claim 20, wherein the second current is configured to cause the AAD to accelerate in speed to prevent backflow into the atrium during systole.

43. The system recited in claim 20, wherein the controller is configured to operate the AAD to pump blood from the atrium through a mitral valve of the patient's heart into the ventricle, and to permit the mitral valve to close to prevent backflow into the atrium during systole.

44. The system recited in claim 20, wherein the heart condition is heart failure.

45. The system recited in claim 20, wherein the atrium is the left atrium and the ventricle is the left ventricle.

46. The system recited in claim 45, wherein the AAD is configured to be positioned in a mitral valve position.

47. The system recited in claim 46, further comprising a sewing cuff for suturing the AAD in the mitral valve position after at least a portion of the mitral valve has been surgically excised.

48. The system recited in claim 45, wherein the AAD is configured to be connected to an annular portion of the mitral valve after a portion of the mitral valve has been surgically excised.

49. The system recited in claim 45, further comprising a sewing cuff for suturing the AAD to the mitral valve.

50. The system recited in claim 45, wherein the AAD is configured to be positioned in the atrium on top of the mitral valve.

51. The system recited in claim 50, wherein the AAD is configured to allow the mitral valve and sub-valvular structures to remain in place.

52. The system recited in claim 50, further comprising a sewing cuff for suturing the AAD to heart structures surrounding mitral valve.

53. The system recited in claim 20, wherein the AAD has an inlet configured to be positioned in the atrium and an outlet configured to discharge blood through a native heart valve into the ventricle.

54. The system recited in claim 53, wherein the outlet is configured to be positioned outside the atrium.

* * * * *